United States Patent
Hathorn

(10) Patent No.: US 10,596,025 B2
(45) Date of Patent: *Mar. 24, 2020

(54) METHOD AND APPARATUS FOR TENSILE COLONOSCOPY COMPRESSION

(71) Applicant: ColoWrap LLC, Durham, NC (US)

(72) Inventor: James P. Hathorn, Durham, NC (US)

(73) Assignee: COLOWRAP, LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/637,529

(22) Filed: Jun. 29, 2017

(65) Prior Publication Data
US 2017/0296374 A1   Oct. 19, 2017

Related U.S. Application Data

(63) Continuation of application No. 13/344,715, filed on Jan. 6, 2012, now Pat. No. 9,724,225.

(51) Int. Cl.
*A61F 5/37* (2006.01)
*A61F 5/00* (2006.01)
(Continued)

(52) U.S. Cl.
CPC .................. *A61F 5/37* (2013.01); *A41C 1/02* (2013.01); *A41C 1/08* (2013.01); *A61F 5/0009* (2013.01);
(Continued)

(58) Field of Classification Search
CPC .. A61F 5/0009; A61F 5/03; A61F 5/37; A61F 13/148; A41C 1/02; A41C 1/08
See application file for complete search history.

(56) References Cited

U.S. PATENT DOCUMENTS

| | | |
|---|---|---|
| 3,115,879 A | 12/1963 | Kaplan |
| 3,120,846 A | 2/1964 | Fletcher |
| (Continued) | | |

FOREIGN PATENT DOCUMENTS

| | | |
|---|---|---|
| CN | 202161367 U | 3/2012 |
| GB | 2 381 732 A | 5/2003 |
| (Continued) | | |

OTHER PUBLICATIONS

European Search Report dated Sep. 2, 2015; Application No. 12864172.7.
(Continued)

*Primary Examiner* — Diane D Yabut
(74) *Attorney, Agent, or Firm* — Arent Fox LLP

(57) ABSTRACT

A method and apparatus for applying pressure to the abdomen of a patient to facilitate the insertion of a colonoscope is characterized by the use of a tensile compression device in the form of an elastic band which is wrapped around the patient's abdomen and secured in place. The tension of the band is adjusted to apply a desired degree of pressure to the patient's abdomen to reduce loops in the patient's colon so that the colonoscope can be fully inserted into the colon with minimal discomfort to the patient. The ends of the device are connected together when the desired degree of tension is obtained so that constant pressure and support are provided to the patient's colon. Addition pressure can be manually applied simultaneously with the pressure from the tensile device to reduce or eliminate more distal loops in the colon.

15 Claims, 2 Drawing Sheets

(51) Int. Cl.
  *A61B 1/31*      (2006.01)
  *A61F 5/03*      (2006.01)
  *A61F 13/14*     (2006.01)
  *A41C 1/02*      (2006.01)
  *A41C 1/08*      (2006.01)

(52) U.S. Cl.
  CPC .............. *A61F 5/03* (2013.01); *A61F 13/148* (2013.01); *A61B 1/31* (2013.01)

(56) References Cited

U.S. PATENT DOCUMENTS

| | | |
|---|---|---|
| 3,554,190 A | 1/1971 | Kaplan |
| 3,902,503 A | 9/1975 | Gaylord, Jr. |
| 4,833,730 A | 5/1989 | Nelson |
| 4,991,234 A | 2/1991 | Greenberg |
| 5,188,585 A | 2/1993 | Peters |
| 5,685,321 A | 11/1997 | Klingenstein |
| 5,885,230 A | 3/1999 | Cherry |
| 6,672,311 B2 | 1/2004 | Rindfleish |
| 8,066,657 B2 | 11/2011 | Frazer |
| 2002/0108617 A1 | 8/2002 | Burton |
| 2011/0087263 A1 | 4/2011 | Arber |

FOREIGN PATENT DOCUMENTS

| | | |
|---|---|---|
| JP | 3051938 U | 6/1998 |
| JP | 2005-021113 A | 1/2005 |
| JP | 2006-314711 A | 11/2006 |
| KR | 200264387 Y1 | 2/2002 |
| WO | WO 95/08308 A1 | 3/1995 |
| WO | WO 96/14811 A1 | 5/1996 |
| WO | WO 97/46180 A1 | 12/1997 |

OTHER PUBLICATIONS

Soper, N. J., et al., Chapter 45: Flexible Endoscopy of the Lower Gastrointestinal Tract, Endoscopic and Laparoscopic Surgery, Lippincott Williams & Wilkins, Philadelphia, PA, pp. 451, 2009.

First Office Action issued in Canadian Patent Application No. 2,869,162 based upon International Patent Application No. PCT/US2012/068492 dated Sep. 26, 2018.

METHOD AND APPARATUS FOR TENSILE COLONOSCOPY COMPRESSION

CROSS-REFERENCE TO RELATED APPLICATIONS

This application is a Continuation of U.S. patent application Ser. No. 13/344,715, now U.S. Pat. No. 9,724,225, filed Jan. 6, 2012. The disclosure of the priority application is incorporated in its entirety herein by reference.

FIELD OF THE INVENTION

The present invention relates to a method and apparatus for compressing and providing support to the abdominal wall to facilitate a colonoscopic examination.

BACKGROUND OF THE INVENTION

A colonoscopy is an examination of the large intestine or colon through the use of a colonoscope. A colonoscope is a flexible, tube-like inspection device having a camera at its end. Colonoscopies are performed for a variety of medical reasons including detection of inflamed tissue, ulcers, abnormal growths or polyps, and colorectal cancer. Colonoscopy as a screening tool to detect colorectal cancer has increased significantly since 2000.

During a colonoscopy, a colonoscope is inserted into a patient's rectum and then advanced to the beginning of the colon (an area known as the cecum) in order to examine the lining of the large intestine. The efficiency and accuracy of this procedure is largely dependent on the ease with which the colonoscope can be advanced. During the procedure, the colon may become over-distended or flopped in unnatural directions creating loops that hinder the advancement of the colonoscope and resulting in patient discomfort, longer examination times, and potentially inaccurate or incomplete screenings.

Currently, the difficulty in advancing the scope has been addressed by utilizing a surgical technician to manually support the patient's colon with pressure. This is time-consuming and dependent on the particular surgical assistant's strength, technique, and endurance, as well as training. Another way to apply differential pressure, particularly in larger patients, is to roll the patient from the left side to a supine or to a prone position. Often this is not an easy task with a sedated patient.

Devices and methods for addressing this problem are known in prior art. For example, the Klingstein U.S. Pat. No. 5,685,321 discloses a method and apparatus for applying external compression to the colon through the use of a corset-like wrap containing a pneumatic, inflatable bladder. The device is wrapped around the patient's abdomen and the bladder, once inflated, applies force to the patient's colon, particularly to the sigmoid colon, in order to facilitate the procedure.

The Rindfleish U.S. Pat. No. 6,672,311 discloses a vest including multiple pneumatic bladders that are selectively inflated by the doctor performing the colonoscopy in order to apply pressure to specific areas of the patient's abdomen.

The Arber U.S. patent application publication No. US 2011/0087263 A1 discloses an abdominal wrap including multiple pneumatic bladders and a counter pressure plate in order to provide downward pressure to a patient's large intestines when the device is inflated.

While the prior devices operate satisfactorily, they require the use of a pneumatic mechanism to apply force to the patient's abdomen. The present invention was developed in order to overcome this and other drawbacks of the prior devices by providing a device in which force and support are generated by tension created when the device is secured around the patient's abdomen. The pressure applied to the patient is the result of the tensile properties of the device and of the material of which the device is composed. Furthermore, the present invention is distinguished from the prior art in that its design purposefully allows a surgical technician to apply additional pressure by manually compressing the abdomen while the device applies simultaneous pressure.

SUMMARY OF THE INVENTION

Accordingly, it is a primary object of the invention to provide a method and apparatus for applying pressure to the abdomen of a patient to ease the passage of a colonoscope during a colonoscopy. More particularly, the invention relates to a non-invasive, external tensile colonoscopy compression device that when applied to a patient, generates tension and exerts pressure upon and provides support to a patient's abdomen region, including the patient's colon, for the purpose of facilitating the advancement of the colonoscope during a colonoscopy.

In a preferred embodiment, the tensile colonoscopy compression device includes an abdominal wrap composed of a thin, flexible, breathable material capable of holding tension when the device is wrapped around a patient's abdomen. The wrap is fastened by a closing mechanism. The device can be between 30 to 70 inches in length and between 4 to 16 inches in width. In one preferred embodiment, the width is between 6 and 8 inches.

The device is formed of a material capable of holding tension in order to exert pressure and provide support to the patient's abdomen. In one embodiment, the material is formed of thin, braided elastic and nylon bands sewn together with a stretchable fiber. In alternative embodiments, the material is a soft, foam-like rubber or neoprene, a manufactured fabric with elastic properties, or a flexible synthetic plastic or vinyl. The material could be disposable in nature, or classified as a medical consumable, in which case the device will be used on only one patient and then discarded.

The closing mechanism is preferably a combination of hook and pyle straps such as a VELCRO® material which are removably and adjustably connected. Other suitable closing mechanisms include a hinged closure, with a hinge on one end of the device through which the other end of the device is passed. The end of the device passed through the hinge has a VELCRO® material patch that adheres to any part of the device. Once this end of the device is passed through the hinge, it is looped back over and fastened.

The tensile colonoscopy compression device according to the invention preferably includes a thin plastic or paper liner that is attached to the inside of the device with fasteners, and rests between the patient's body and the device.

In yet another aspect, the invention relates to a method for compressing and supporting a patient's colon during a colonoscopy. The compression device is applied to the patient prior to sedation, thereby allowing the patient to provide the doctor with feedback regarding his or her comfort level and obviating the risk of over-compression. If greater pressure is needed after the patient has been sedated and the procedure has begun, the doctor may instruct a surgical technician to manually apply location-specific pressure through the device given its thin construction.

BRIEF DESCRIPTION OF THE FIGURES

Other objects and advantages of the present invention will become apparent from a study of the following specification when viewed in the light of the accompanying drawing, in which.

DETAILED DESCRIPTION

Figure 1:
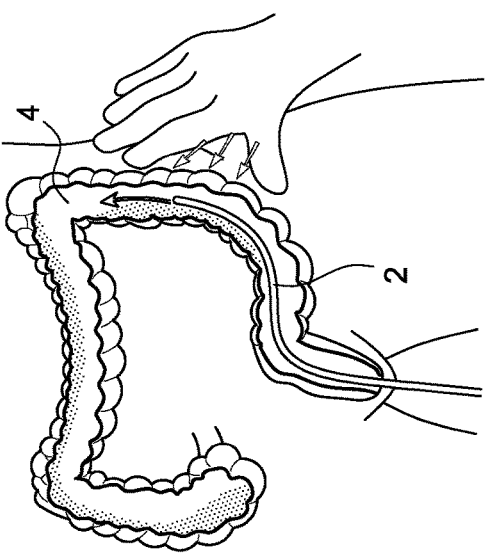
FIG. 1 is a schematic view of a colon with a colonoscope partially inserted therein.
Figure 2:
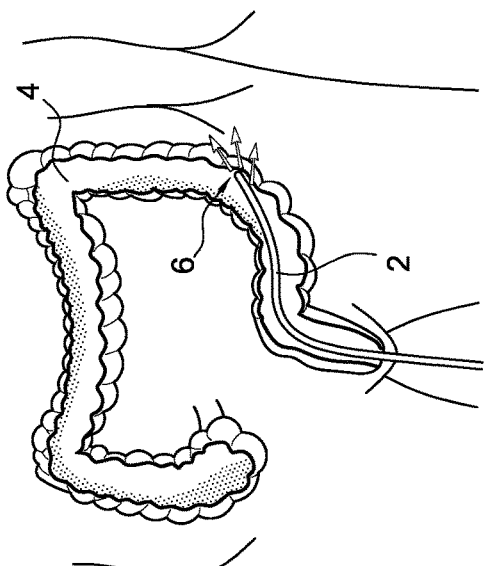
FIG. 2 is a schematic view of a colon in which a sigmoid loop has developed due to an attempt to advance the colonoscope against an unsupported colon wall.
Figure 3:
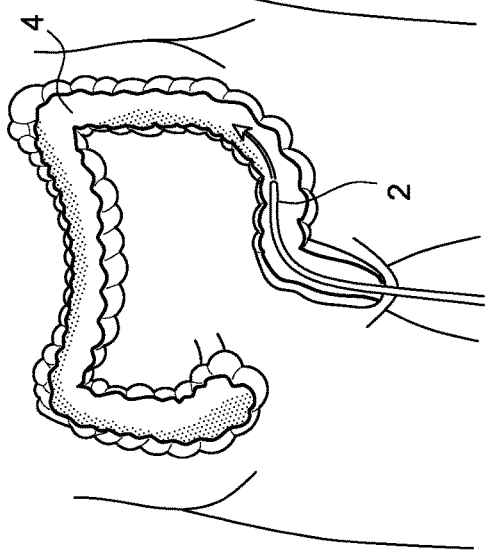
FIG. 3 is a schematic view of a colon showing the manual application of pressure to the colon to facilitate insertion of a colonoscope.

Referring first to FIGS. 1-3, there is shown in schematic form the sequence of steps of performing a colonoscopy. In FIG. 1, a colonoscope 2 is inserted into the patient's rectum and advanced to the cecum which is at the beginning of the colon 4. As the colonoscope is advanced through the colon, it often engages an area 6 where the colon is distended or looped as shown in FIG. 2. In such areas, it is difficult to advance the colonoscope which causes discomfort to the patient and increases the time required for the colonoscopy. In order to reduce the distended or looped area, a surgical assistant presses on the abdomen of the patient in the area where the colonoscope has become inhibited in order to straighten the colon to allow the passage of the colonoscope as shown in FIG. 3.

Figure 4:
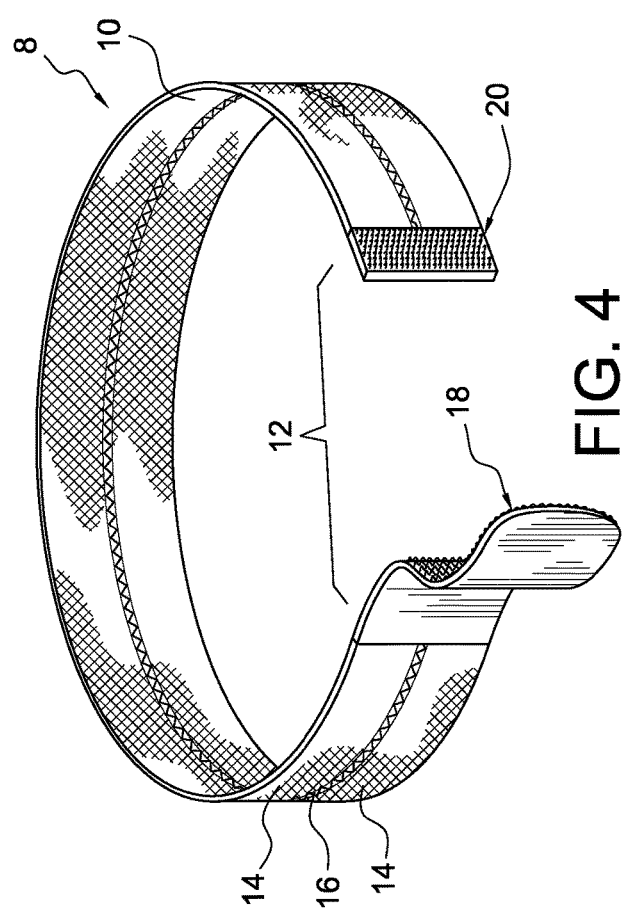
FIG. 4 is a perspective view of a tensile colonoscopy compression device according to a preferred embodiment of the invention.
Figure 5:
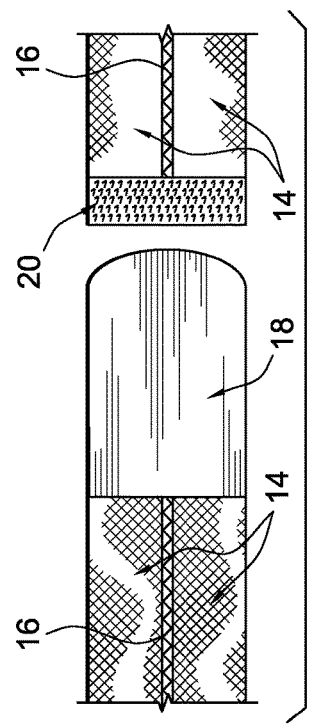
FIG. 5 is a detailed plan view of a closing mechanism and wrap construction of the tensile colonoscopy compression device of FIG. 3.

The tensile colonoscopy compression device 8 according to the invention is used to apply pressure and support to the abdomen of a patient undergoing a colonoscopy is shown in FIGS. 4 and 5. The device 8 is formed of an elongated tensile band or wrap 10 of sufficient length for placement around a patient's abdomen. A closing mechanism 12 is provided at the end of the band to secure the device around the patient so that it provides the desired amount of force.

The tensile wrap 10 preferably has a circumferential length between 15 and 75 inches in order to accommodate varying abdominal girths in patients. The preferred width of the wrap 10 is between 6 and 9 inches, although widths of between 4 and 16 inches may be used depending on the size of the patient. Because the tensile wrap 10 is used to generate pressure upon the patient's abdomen, it is preferred that the wrap be constructed of a material with elastic properties that is capable of holding tension. The degree of elasticity of the wrap will vary in accordance with the material used for the band. The wrap may be formed from a single band or composed of several bands of woven, elastic nylon fabric 14, each approximately 3 inches wide and spaced approximately 0.2 inches apart from one another as shown in FIG. 4. These bands are sewn together with elastic stitching 16 that bridges the space between each band. In the embodiment shown in FIGS. 4 and 5, two elongated bands 14 are provided. In the embodiment shown in FIGS. 6-8, three spaced elongated bands are provided.

In the preferred embodiment, the closing mechanism 12 is a VELCRO® fastener including a pile pad 18 sewn onto one end of the wrap 10 and a hooked strip 20 sewn onto the other end of the wrap 10. The pad and strip are both of generally the same width as the wrap. The pad has a length of about six inches and the strip has a length of about two inches. To fasten the wrap 10, the pad 18 is pulled over top and pressed into the strip 20, which secures the two ends of the wrap 10 together.

Other types of closing mechanisms may be provided, including for example a hinged clamp, a strap and buckle arrangement, or a strap and loop arrangement. In addition, where the wrap is formed of a woven material, the closing mechanism may comprise a hooked portion connected at one end of the wrap. The wrap is wound about a patient's abdomen with the hooked end overlapping the wrap and fastening directly to the woven material of the wrap. It is important that the closing mechanism be adjustable in order to vary the pressure and support provided to the patient as will be developed in greater detail below.

Figure 6:
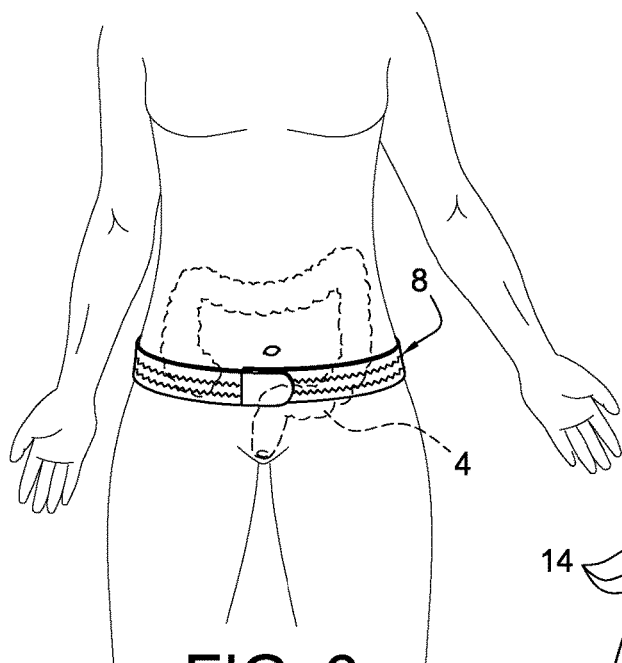
FIG. 6 is a schematic illustration of the tensile colonoscopy compression device of FIG. 3 applied to a patient.
Figure 7:
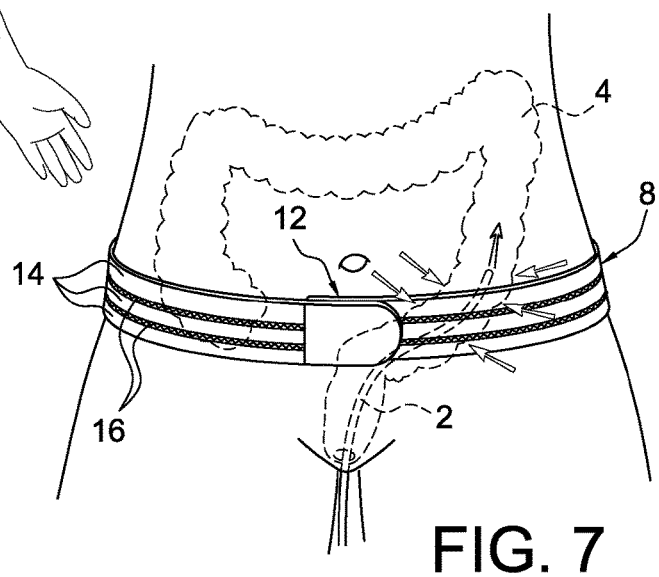
FIG. 7 is a schematic illustration of a patient's colon with a tensile colonoscopy compression device according to the invention applied to the patient's abdomen.
Figure 8:
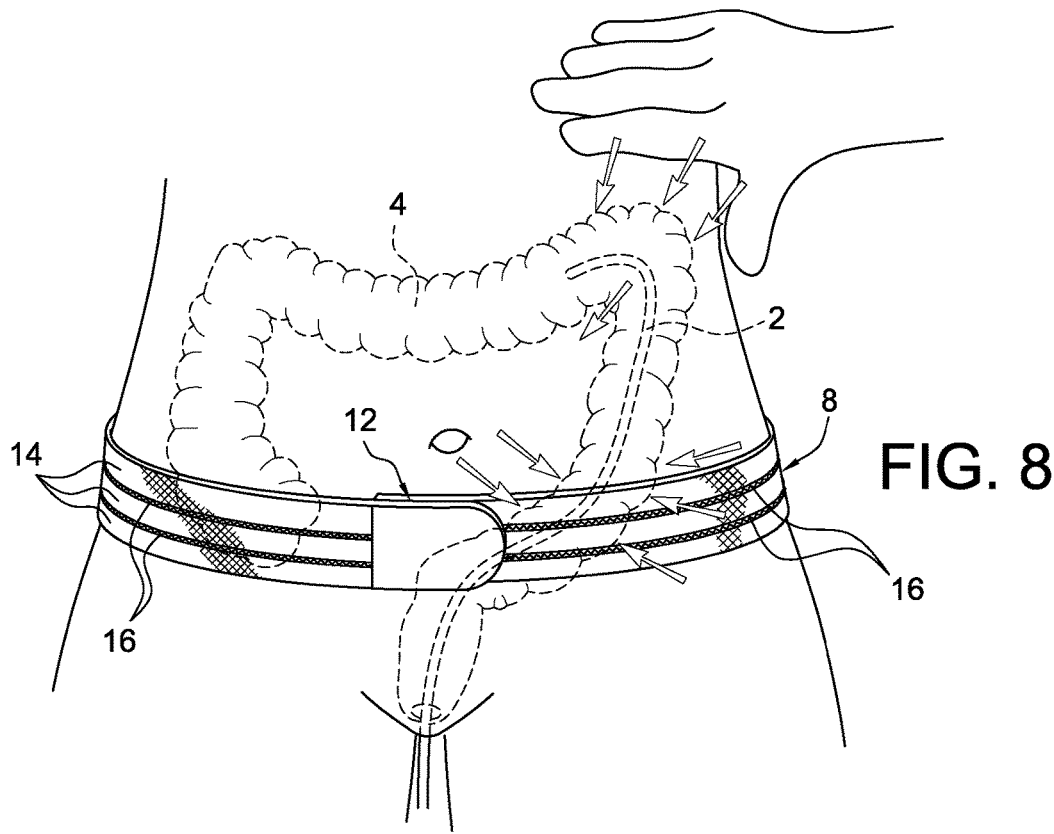
FIG. 8 is schematic illustration similar to FIG. 7 but showing the application of manual pressure to the abdomen to supplement that applied by the tensile colonoscopy compression device.

In use, the tensile colonoscopy compression device 8 according to the invention is applied to the patient as shown in FIGS. 6-8. The device is applied just before the patient is sedated as the patient lies on a stretcher in the colonoscopy room. The tensile colonoscopy compression device 8 is pulled under the patient while the patient is in a supine position and the wrap 10 is secured evenly around the lower abdomen via the closing mechanism 12. As shown in FIG. 6, the closing mechanism 12 is preferably situated in the front part of the patient's body in such a way that it is readily accessible to the surgical technician. The bottom of the wrap 10 is preferably aligned with the top of the patient's hips, and the top of the wrap 10 is positioned at or just below the level of the patient's umbilicus. Once in position, the tensile colonoscopy compression device 8 is adjusted to the desired level of tension by loosening or tightening the closing mechanism 2.

The tensile colonoscopy compression device 8 is applied to the patient before the patient is sedated so that the patient is able to provide feedback to the doctor regarding his or her level of comfort as the tension of the device 8 is adjusted. The patient is advised that the device 8 should exert pressure to the abdomen, but that at no time should it cause discomfort.

Once the device 8 is secured around the patient's lower abdomen at the desired level of tension, sedative medication is then delivered through the patient's IV and the patient is rolled into a left lateral position for the insertion of the colonoscope. Referring to FIG. 7, as the colonoscope is advanced into the patient's left lower colon, or sigmoid colon, the patient's abdomen is compressed and supported by the device 8 with gentle but adequate pressure to prevent a sigmoid loop from forming. This enables the doctor to advance the colonoscope more quickly with less distension or stretching of the colon. The pressure applied by the tensile colonoscopy compression device 8 is sufficient to prevent loops from forming in the colon, thereby allowing the colonoscope to advance through the patient's colon without causing discomfort.

Even with the tensile colonoscopy compression device in place, a more proximal loop may form in the colon, for instance in the left or right upper quadrants (the splenic or the hepatic flexures) as shown in FIG. 8. The tensile colonoscopy compression device 8 according to the invention allows a surgical technician to apply pressure manually while the patient's abdomen remains simultaneous compressed by the device. Without the use of the tensile colonoscopy compression device, such simultaneous and uniform pressure would be hard to achieve and maintain due to limitations in the strength, endurance, training, and understanding of the procedure by the attending surgical technician.

In the preferred embodiment, once the colonoscope reaches the patient's cecum and abdominal compression is no longer needed, the tensile colonoscopy compression device 8 is released with a simple pull upon the top side of the closing mechanism 12 and the patient's colon is then examined as the scope is slowly withdrawn.

It will be appreciated that other suitable elastic materials may be used in place of nylon to form the wrap or band. Suitable alternatives include soft, foam-like rubber or neoprene, a manufactured fabric with elastic properties, or a flexible synthetic plastic or vinyl. The device may include a removable liner (not shown) which is arranged between the band and the patient. The liner is replaced for subsequent use of the compression device on other patients. Alternatively, the elastic material could be disposable in nature, or classified as a medical consumable, in which case the device will be used on only one patient and then discarded.

While the preferred forms and embodiments of the invention have been illustrated and described be apparent to those of ordinary skill in the art that various changes and modifications may be made without deviating from the inventive concepts set forth above.

What is claimed is:

1. A neoprene colonoscopy compression apparatus for applying pressure to the abdomen of a patient in order to reduce loops in the patient's colon and facilitate passage of a colonoscope during a colonoscopy, comprising:
    an elongated band of elastic material comprising neoprene and configured for placement around the abdomen of the patient, wherein the elongated band is capable of contracting across the abdomen of the patient to apply a selected degree of constant pressure, wherein the selected degree of constant pressure is applied to and across the abdomen through contraction of at least a portion of the elongated band of elastic material that extends across the abdomen of the patient; and
    a closure connected with at least one end of said elongated band for connecting said one end of the band with another portion of the band under a desired degree of tension, whereby when said band is positioned around the abdomen of a patient and said closure is operated to connect the band together,
    wherein the neoprene colonoscopy compression apparatus is configured to apply the selected degree of constant pressure and support to and across the patient's abdomen across a surface of the elongated band that extends across the abdomen of the patient through the contraction of the elongated band of elastic material in order to reduce loops in the patient's colon and facilitate passage of the colonoscope during the colonoscopy.

2. The neoprene colonoscopy compression apparatus of claim 1, further comprising a liner on a side of the elongated band of elastic material that is configured to be placed around the abdomen of the patient.

3. The neoprene colonoscopy compression apparatus of claim 1, wherein said closure comprises a hook member configured to adhere to any part of the elongated band of elastic material.

4. The neoprene colonoscopy compression apparatus of claim 1, wherein the elongated band of elastic material further comprises a woven material, and
    wherein the closure comprises a hook member configured to overlap the elongated band of elastic material and fasten directly to the woven material along any position of the elongated band of elastic material.

5. The neoprene colonoscopy compression apparatus of claim 1, wherein said closure is adjustable to vary the tension applied by the band to the patient.

6. The neoprene colonoscopy compression apparatus of claim 5, wherein said closure comprises a pile member connected with one end of said elongated band of material and a hook member connected with the other end of said elongated band of material, said hook and pile members cooperating to interconnect and join the ends of said elongated band of material.

7. The neoprene colonoscopy compression apparatus of claim 1, wherein the apparatus is configured to apply the selected degree of constant pressure and support to the patient's abdomen through contraction of the elongated band of elastic across the patient's abdomen in an area extending between the hips and umbilicus of the patient, without extending above the umbilicus of the patient.

8. The neoprene colonoscopy compression apparatus of claim 1, wherein the elongated band of elastic material is configured to have a first edge aligned approximately with the top of the patient's hips when an opposite edge of the band of elastic material is positioned approximately at a level of the patient's umbilicus.

9. The neoprene colonoscopy compression apparatus of claim 1, wherein the constant pressure is a diffuse pressure applied to the patient's abdomen through contraction of the elongated band of elastic material, and wherein the diffuse pressure of the contraction of the elongated band is sufficient to reduce loops in the patient's colon and facilitate passage of the colonoscope during the colonoscopy.

10. The neoprene colonoscopy compression apparatus of claim 1, wherein the elongated band of elastic material is configured for placement around the abdomen of the patient such that the band extends from the hips of the patient to the umbilicus of the patient.

11. The neoprene colonoscopy compression apparatus of claim 1, wherein the elongated band of elastic material is configured to allow manual application of location-specific pressure through the neoprene colonoscopy compression apparatus.

12. The neoprene colonoscopy compression apparatus of claim 1, wherein the closure comprises a strap and buckle arrangement.

13. The neoprene colonoscopy compression apparatus of claim 1, wherein the closure comprises a strap and loop arrangement.

14. The neoprene colonoscopy compression apparatus of claim 1, wherein the closure comprises a hinged clamp arrangement.

15. The neoprene colonoscopy compression apparatus of claim 1, wherein when properly positioned, the closure is positioned at the patient's abdomen and is readily accessible by a technician throughout the colonoscopy procedure while the patient is in a left lateral position.

* * * * *